United States Patent
Kim et al.

(10) Patent No.: US 9,795,313 B2
(45) Date of Patent: Oct. 24, 2017

(54) BIOELECTRODE, AND METHOD AND APPARATUS FOR PROCESSING BIOSIGNAL USING THE SAME

(71) Applicants: Samsung Electronics Co., Ltd., Suwon-si (KR); SNU R&DB Foundation, Seoul (KR)

(72) Inventors: Youn Ho Kim, Seoul (KR); Jee Hoon Kim, Gwacheon-si (KR); Kwang Suk Park, Seoul (KR); Jeong Su Lee, Seoul (KR); Yong Gyu Lim, Seoul (KR)

(73) Assignees: Samsung Electronics Co., Ltd., Suwon-si (KR); SNU R&DB Foundation, Seoul (KR)

( * ) Notice: Subject to any disclaimer, the term of this patent is extended or adjusted under 35 U.S.C. 154(b) by 138 days.

(21) Appl. No.: 14/712,110

(22) Filed: May 14, 2015

(65) Prior Publication Data
US 2015/0366479 A1     Dec. 24, 2015

(30) Foreign Application Priority Data

Jun. 23, 2014  (KR) ........................ 10-2014-0076780

(51) Int. Cl.
*G09G 5/00*  (2006.01)
*A61B 5/04*  (2006.01)
(Continued)

(52) U.S. Cl.
CPC ........ *A61B 5/04012* (2013.01); *A61B 5/0478* (2013.01); *A61B 5/04085* (2013.01);
(Continued)

(58) Field of Classification Search
CPC ... A61B 5/04012; A61B 5/0492; A61B 5/681; A61B 5/04085; A61B 2562/0209;
(Continued)

(56) References Cited

U.S. PATENT DOCUMENTS 4,367,745 A * 1/1983 Welage ................. A61B 18/16
                                                                 252/511
4,539,996 A * 9/1985 Engel ................. A61B 5/04087
                                                                 252/500
(Continued)

FOREIGN PATENT DOCUMENTS

DE     10 2012 014219 A1    8/2013
EP        1 704 894 A2      9/2006
(Continued)

OTHER PUBLICATIONS

Extended European Search Report dated Oct. 30, 2015 in counterpart European Application No. 15171760.0 (6 pages in English).

*Primary Examiner* — Prabodh M Dharia
(74) *Attorney, Agent, or Firm* — NSIP Law

(57) ABSTRACT

A bioelectrode including a plate, a first electrode disposed on a first side of the plate, and a second electrode disposed on the first side of the plate and separate from the first electrode. The bioelectrode further includes a first guard portion disposed on a second side of the plate, a second guard portion disposed on the second side of the plate and separate from the first guard portion, and a preamplifier configured to output a voltage signal based on a biosignal measured between the first electrode and the second electrode.

20 Claims, 10 Drawing Sheets

(51) Int. Cl.
*A61B 5/0492* (2006.01)
*A61B 5/00* (2006.01)
*A61B 5/0408* (2006.01)
*A61B 5/0478* (2006.01)
*G06F 3/01* (2006.01)
*A61B 5/11* (2006.01)

(52) U.S. Cl.
CPC .......... *A61B 5/0492* (2013.01); *A61B 5/1126* (2013.01); *A61B 5/681* (2013.01); *G06F 3/011* (2013.01); *G06F 3/015* (2013.01); *G06F 3/017* (2013.01); *A61B 5/0002* (2013.01); *A61B 5/7203* (2013.01); *A61B 5/7225* (2013.01); *A61B 2562/0209* (2013.01); *A61B 2562/0214* (2013.01); *A61B 2562/04* (2013.01); *A61B 2562/16* (2013.01); *A61B 2562/182* (2013.01)

(58) Field of Classification Search
CPC . A61B 2562/04; A61B 2562/16; G06F 3/015; G06F 3/017; G06F 3/011
USPC .................. 345/156–184; 600/393, 547, 513; 607/42, 46, 72, 142; 324/686
See application file for complete search history.

(56) References Cited

U.S. PATENT DOCUMENTS

| | | | | |
|---|---|---|---|---|
| 5,069,223 | A * | 12/1991 | McRae | A61B 5/053 600/547 |
| 5,466,256 | A * | 11/1995 | McAdams | A61N 1/0492 600/391 |
| 6,647,292 | B1 | 11/2003 | Bardy et al. | |
| 2003/0120329 | A1 | 6/2003 | Getsla et al. | |
| 2004/0140209 | A1* | 7/2004 | Choi | B82Y 30/00 204/403.01 |
| 2005/0054941 | A1* | 3/2005 | Ting | A61B 5/0408 600/529 |
| 2006/0276702 | A1* | 12/2006 | McGinnis | A61B 5/0408 600/372 |
| 2007/0255152 | A1* | 11/2007 | Park | A61B 5/0428 600/513 |
| 2011/0245702 | A1* | 10/2011 | Clark | A61B 5/04284 600/523 |
| 2012/0245444 | A1* | 9/2012 | Otis | A61B 5/1486 600/345 |
| 2013/0001090 | A1* | 1/2013 | Rubinson | A61N 1/04 205/118 |
| 2013/0197338 | A1* | 8/2013 | Yu | A61N 1/36021 600/377 |
| 2013/0257688 | A1* | 10/2013 | Yamazaki | G02B 27/01 345/7 |
| 2013/0338529 | A1* | 12/2013 | Ishijima | A61B 5/7203 600/547 |
| 2014/0051945 | A1* | 2/2014 | Sarasua | A61B 5/0402 600/301 |
| 2014/0226083 | A1* | 8/2014 | Dunphy | G06F 3/044 349/12 |
| 2015/0157269 | A1* | 6/2015 | Lisogurski | A61B 5/0205 600/301 |
| 2015/0173639 | A1* | 6/2015 | Ichida | A61B 5/0408 600/397 |
| 2015/0216044 | A1* | 7/2015 | Tamagawa | H01C 7/00 361/752 |
| 2015/0217082 | A1* | 8/2015 | Kang | G06F 19/3431 600/28 |
| 2015/0265412 | A1* | 9/2015 | Arakawa | A61F 5/013 623/64 |
| 2015/0335288 | A1* | 11/2015 | Toth | A61B 5/6833 600/373 |
| 2015/0367124 | A1* | 12/2015 | Noda | A61B 5/0478 607/116 |
| 2016/0057565 | A1* | 2/2016 | Gold | H04W 4/008 455/41.1 |
| 2016/0145669 | A1* | 5/2016 | Curchoe | C12Q 1/004 361/502 |
| 2016/0278736 | A1* | 9/2016 | Hamilton | A61B 8/06 |

FOREIGN PATENT DOCUMENTS

| | | |
|---|---|---|
| JP | 2003-275185 A | 9/2003 |
| JP | 2003-287550 A | 10/2003 |
| JP | 2007-159722 A | 6/2007 |
| JP | 5280446 B2 | 5/2013 |
| KR | 2002-0009180 A | 2/2002 |
| KR | 10-0636826 B1 | 10/2006 |
| KR | 10-2012-0102201 A | 9/2012 |
| WO | WO 2012/149466 A2 | 11/2012 |

* cited by examiner

BIOELECTRODE, AND METHOD AND APPARATUS FOR PROCESSING BIOSIGNAL USING THE SAME

CROSS-REFERENCE TO RELATED APPLICATION

This application claims the benefit under 35 USC 119(a) of Korean Patent Application No. 10-2014-0076780, filed on Jun. 23, 2014, in the Korean Intellectual Property Office, the entire disclosure of which is incorporated herein by reference for all purposes.

BACKGROUND

1. Field

The following description relates to a bioelectrode, and a method and an apparatus for processing a biosignal using the bioelectrode.

2. Description of Related Art

When a cell is stimulated, an active reaction may occur, and ions may move in a cell membrane on a surface of the cell. Since a body tissue and a body fluid have a characteristic of electrical conductivity, a current may flow around an activated cell. A bioelectrode may be used to measure a biosignal such as an electrocardiogram (ECG), an electromyogram (EMG), an electroencephalogram (EEG), and the like. The bioelectrode may perform a function of a transducer to convert a current occurring due to movements of the ions in the body, into a current occurring due to a free electron. When the bioelectrode is attached to a predetermined part of the body, a biopotential reflecting an electrical phenomenon of the body may be detected. In general, the biopotential may have a low intensity, be easily affected by noise, and include a predetermined frequency component.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an embodiment, there is provided a bioelectrode including a plate; electrodes disposed at a first side of the plate and separate from one another and configured to measure a biosignal; and guard portions disposed at a second side of the plate and separate from one another.

The electrodes may include a first electrode disposed on the first side of the plate and a second electrode disposed on the first side of the plate and separate from the first electrode, and the guard portions may include a first guard portion disposed on the second side of the plate and a second guard portion disposed on the second side of the plate and separate from the first guard portion.

The bioelectrode may also include a preamplifier configured to output a voltage signal based on a biosignal measured between the first electrode and the second electrode.

The first guard portion may be disposed vertically separate from the first electrode; and the second guard portion may be disposed vertically separate from the second electrode.

The first guard portion and the second guard portion may be configured to reduce external noise affecting the biosignal measured between the first electrode and the second electrode.

The first guard portion and the second guard portion may include a conductive material, and are electrically connected to the preamplifier.

The bioelectrode may also include a shield disposed externally to the preamplifier, the first guard portion, and the second guard portion.

The shield may be configured to form an air layer between the shield and the plate.

The shield may include a conductive material, and is connected to ground.

One of the electrodes and the guard portions may be disposed between the plate and an insulation layer.

One of the electrodes and the guard portions may be disposed internally into the plate.

The first electrode and the second electrode may be configured to measure an electromyogram of a user without making direct electrical contact with a body of the user.

In accordance with another embodiment, there is provided a biosignal processing apparatus including a bioelectrode configured to measure a biosignal without making direct electrical contact with a body of a user; and a biosignal processing portion configured to filter the biosignal, and amplify the filtered biosignal, wherein the bioelectrode comprises electrodes disposed on a first side of a plate and separate from one another, and guard portions disposed on a second side of the plate and separate from one another.

The electrodes may include a first electrode and a second electrode; the guard portions may include a first guard portion and a second guard portion; the first guard portion may be disposed to vertically overlap the first electrode; and the second guard portion may be disposed to vertically overlap the second electrode.

The bioelectrode may further include a preamplifier configured to output a voltage signal based on a biosignal measured between the electrodes based on an input impedance.

The bioelectrode may further include a shield disposed externally to the guard portions and electrically separate from the guard portions.

The apparatus may also include a signal converter configured to convert the biosignal output from the biosignal processing portion, into a digital signal; and an interface configured to transmit the digital signal to an external area.

The biosignal processing apparatus may be configured to operate in a wearable device.

In accordance with an embodiment, there is provided a biosignal processing apparatus including a bioelectrode configured to measure a biosignal, using electrodes disposed on a first side of a plate and separate from one another, without making direct electrical contact with a body of a user; and a control signal generator configured to generate a control signal to be used to control an external device based on the biosignal.

The bioelectrode may further include guard portions disposed on a second side of the plate and separate from one another; and a shield disposed externally to the plate and connected to ground.

Other features and aspects will be apparent from the following detailed description, the drawings, and the claims.

Figure 1:
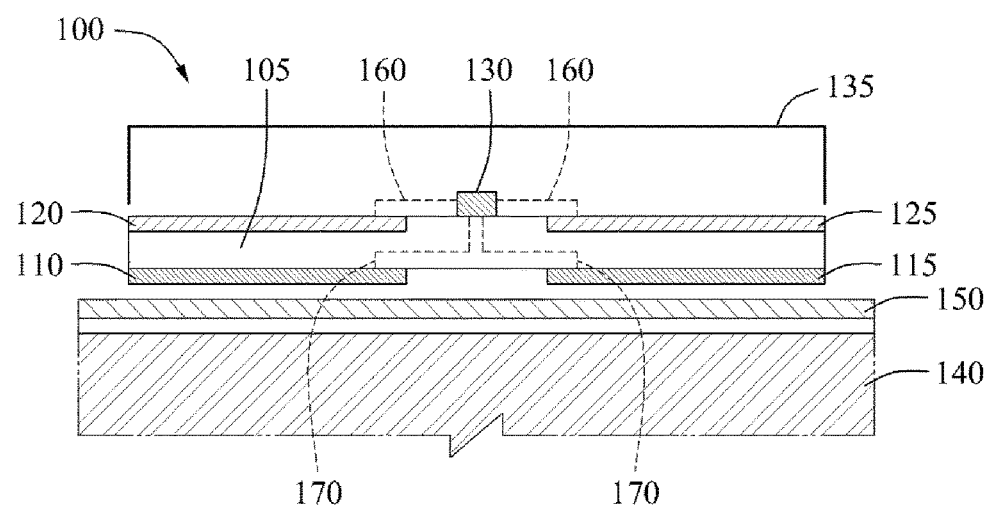
FIG. 1 is a diagram illustrating an example of a bioelectrode.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Unless indicated otherwise, a statement that a first layer is "on" a second layer or a substrate is to be interpreted as covering both a case where the first layer is directly contacts the second layer or the substrate, and a case where one or more other layers are disposed between the first layer and the second layer or the substrate.

The spatially-relative expressions such as "below", "beneath", "lower", "above", "upper", and the like may be used to conveniently describe relationships of one device or elements with other devices or among elements. The spatially-relative expressions should be understood as encompassing the direction illustrated in the drawings, added with other directions of the device in use or operation. Further, the device may be oriented to other directions and accordingly, the interpretation of the spatially-relative expressions is based on the orientation.

The expression such as "first conductivity type" and "second conductivity type" as used herein may refer to the conductivity types such as N or P types which are opposed to each other, and an example explained and exemplified herein encompasses complementary examples thereof.

FIG. 1 is a diagram illustrating an example of a bioelectrode 100. The bioelectrode 100 measures a biosignal from a body 140 of a user. The bioelectrode 100 may measure the biosignal, for example, an electromyogram (EMG), an electrocardiogram (ECG), and an electroencephalogram (EEG). For example, to measure the EMG, the bioelectrode 100 may measure an action potential occurring due to a contraction of muscles, using a plurality of electrodes included in the bioelectrode 100.

The bioelectrode 100 may measure the biosignal of the body 140 when the bioelectrode 100 is in direct or indirect electrical contact with a skin of the user. For example, the biosignal may be measured by attaching the bioelectrode 100 to clothes 150 in a state in which the user is wearing the clothes 150. When a capacitance is formed between the skin of the user and the electrodes included in the bioelectrode 100, the bioelectrode 100 may measure an electrical signal occurring due to movements of ions in the body 140 of the user in the state in which the user is wearing the clothes 150. The user may experience less inconvenience by measuring the biosignal without making direct contact with the skin. To measure the biosignal without making direct electrical contact with the skin of the body 140, a displacement current may be measured. A potential change occurring on a surface of the body 140 may cause a voltage change in an electrode of the bioelectrode 100. The displacement current may refer to a current generated in response to the voltage change.

A general bioelectrode may include a single electrode, and the biosignal may be measured using a plurality of bioelectrodes. In FIG. 1, the bioelectrode 100 includes a plurality of electrodes, and thus, the biosignal may be measured using a single bioelectrode, for example, the bioelectrode 100. In the bioelectrode 100, a V+ electrode and a V− electrode may be implemented in a single module. Based on a configuration of the bioelectrode 100 including the plurality of electrodes, a bioelectrode may be provided in a reduced size to measure a biosignal.

Referring to FIG. 1, the bioelectrode 100 includes a plate 105, the plurality of electrodes including a first electrode 110 and a second electrode 115, a plurality of guard portions including a first guard portion 120 and a second guard portion 125, a preamplifier 130, and a shield 135.

The plate 105 is a member that supports the plurality of electrodes, the plurality of guard portions, and the preamplifier 130. For example, the plate 105 may be provided in a form of a printed circuit board (PCB), a pad, a patch, and an insulation shield made of an insulation material.

The plurality of electrodes includes the first electrode 110 and the second electrode 115. For example, the first electrode 110 may be the V+ electrode, and the second electrode 115 may be the V− electrode. The first electrode 110 and the second electrode 115 measure a biosignal from the body 140 of the user. The first electrode 110 and the second electrode 115 may measure an electrical signal occurring due to a flow of ions in the body 140 of the user. The first electrode 110 and the second electrode 115 may measure a biosignal, such as an EMG, from the body 140 without making direct electrical contact with the body 140.

The first electrode 110 is disposed on a first side of the plate 105. For example, the first electrode 110 may be disposed internally into the plate 105 or disposed on a lower surface of the plate 105. The second electrode 115 is disposed on the first side of the plate 105 and disposed separate from the first electrode 110. For example, the second electrode 115 may be disposed internally into the plate 105 or disposed on the lower surface of the plate 105. The first electrode 110 and the second electrode 115 are disposed on an identical plane. In an example, the bioelectrode 100 may also include a first insulation layer (not shown), and the first electrode 110 and the second electrode 115 may be disposed between the plate 105 and the first insulation layer. The first insulation layer may prevent the first electrode 110 and the second electrode 115 from being directly exposed to an outside environment of the bioelectrode 100. The first electrode 110 and the second electrode 115 are electrically connected to the preamplifier 130, and transfer a measured electrical signal to the preamplifier 130.

The plurality of guard portions includes the first guard portion 120 and the second guard portion 125. The first guard portion 120 and the second guard portion 125 may reduce external noise affecting a biosignal measured between the first electrode 110 and the second electrode 115. When the biosignal is measured without making direct electrical contact with the skin of the user, the bioelectrode 100 may be influenced to a relatively great degree by the external noise or a motion artifact due to a high impedance of a medium, for example, the clothes 150, between the bioelectrode 100 and the body 140 of the user. The first guard portion 120 and the second guard portion 125 may reduce an influence of external noise originating from a direction opposite to a direction in which the biosignal is measured. Also, the first guard portion 120 and the second guard portion 125 may be used to reduce an influence of a parasitic capacitance such as a stray capacitance.

The first guard portion 120 is disposed on a second side of the plate 105. For example, the first guard portion 120 may be disposed internally into the plate 105 or disposed on an upper surface of the plate 105. The first guard portion 120 is disposed vertically separate from the first electrode 110. The second guard portion 125 is disposed on the second side of the plate 105 and disposed separate from the first guard portion 120. For example, the second guard portion 125 may be disposed internally into the plate 105 or disposed on the upper surface of the plate 105. The second guard portion 125 is disposed vertically separate from the second electrode 115. The first guard portion 120 and the second guard portion 125 are disposed on an identical plane. In an example, the bioelectrode 100 may also include a second insulation layer (not shown), and the first guard portion 120 and the second guard portion 125 may be disposed between the plate 105 and the second insulation layer. The first guard portion 120 and the second guard portion 125 may include a conductive material, and are electrically connected to the preamplifier 130.

The shield 135 may reduce external noise affecting the biosignal measured between the first electrode 110 and the second electrode 115. The shield 135 may reduce external noise affecting at least one of the first electrode 110, the second electrode 115, and signal lines 160 and 170 included in the bioelectrode 100. The signal line 160 includes a signal line connecting the first guard portion 120 and the preamplifier 130, and a signal line connecting the second guard portion 125 and the preamplifier 130. The signal line 170 includes a signal line connecting the first electrode 110 and the preamplifier 130, and a signal line connecting the second electrode 115 and the preamplifier 130. The shield 135 may prevent the external noise from affecting the bioelectrode 100. In addition, the first guard portion 120 and the second guard portion 125 may prevent the external noise from affecting the biosignal. By doubly blocking the external noise using the shield 135, the first guard portion 120, and the second guard portion 125, an increased quality of a biosignal may be achieved.

The shield 135 is disposed externally to the first guard portion 120, the second guard portion 125, and the preamplifier 130. The shield 135 may include the conductive material, and may be connected to a ground. The shield 135 is electrically separate from the first guard portion 120 and the second guard portion 125, and forms an air layer between the shield 135 and the plate 105. In an example, the shield 135 may be supported by a supporting member (not shown) disposed on the upper surface of the plate 105.

The preamplifier 130 outputs a voltage signal based on the biosignal measured between the first electrode 110 and the second electrode 115. The preamplifier 130 may be used to perform an impedance conversion or to amplify the biosignal measured between the first electrode 110 and the second electrode 115. The preamplifier 130 may amplify an infinitesimal biosignal input through a displacement current without making direct contact, and convert the amplified biosignal into the voltage signal. The preamplifier 130 may have a relatively high input impedance to convert an infinitesimal biosignal measured based on a non-contact method that avoids direct electrical contact with a skin of a user, into a voltage signal having a high gain value. For example, when an EMG signal is measured using the bioelectrode 100 based on the non-contact method, the bioelectrode 100 may have a high input impedance to normally acquire the biosignal because the clothes 150 have an impedance ranging from tens of mega-ohms to hundreds of mega-ohms, and the EMG signal has a small intensity. To normally acquire the biosignal measured based on the non-contact method, the preamplifier 130 may provide the high input impedance to the bioelectrode 100. The preamplifier 130 is shielded by the shield 135 disposed externally to the preamplifier 130.

Figure 2:
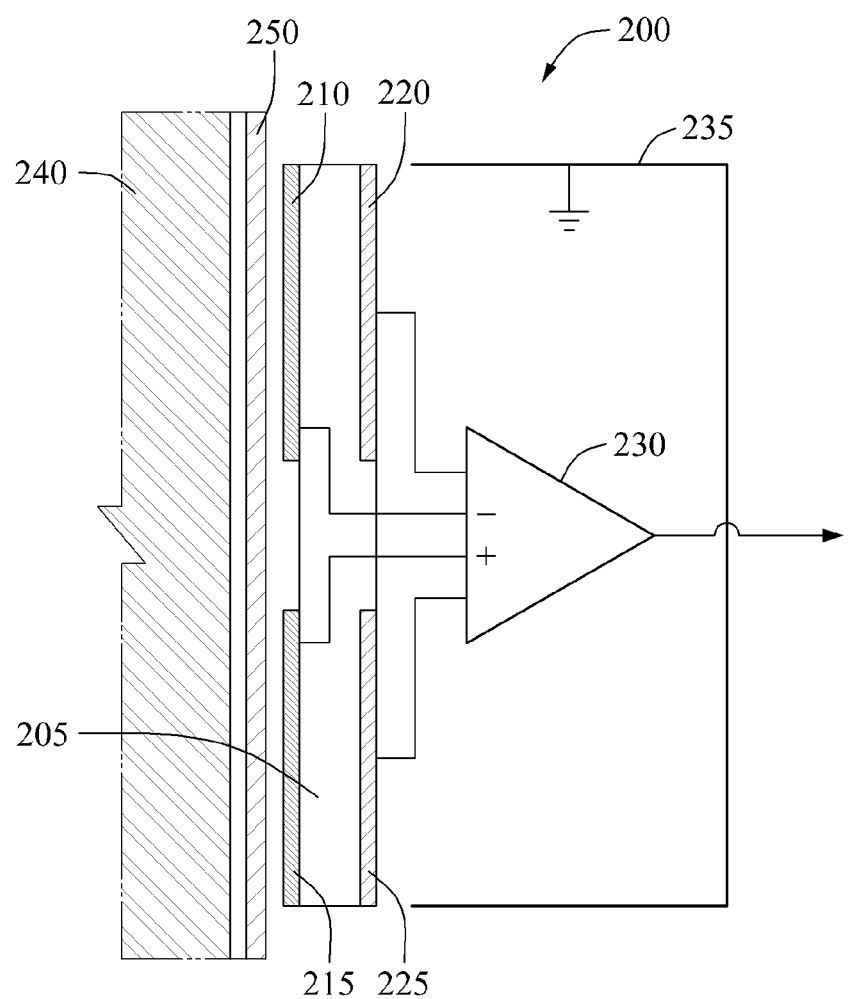
FIG. 2 is a diagram illustrating an example of measuring a biosignal using a bioelectrode.

FIG. 2 is a diagram illustrating an example of measuring a biosignal using a bioelectrode 200. The bioelectrode 200 measures a biosignal of a user based on a non-contact method that avoids direct electrical contact with a body 240 of the user. The bioelectrode 200 measures the biosignal of the body 240 by measuring a displacement current caused due to a potential changed based on an expression of the body 240 in a state in which the user is wearing clothes 250. The bioelectrode 200 includes a first electrode 210 and a second electrode 215 that are disposed on a first side of a plate 205 and disposed separate from one another. The bioelectrode 200 includes a first guard portion 220 and a second guard portion 225 that are disposed on a second side of the plate 205 and disposed separate from one another. The bioelectrode 200 includes a preamplifier 230 and a shield 235 that are disposed externally to the preamplifier 230 to shield the preamplifier 230. The shield 235 shields the first guard portion 220 and the second guard portion 225 as well as the preamplifier 230, and may reduce an influence of external noise. The first guard portion 220 and the second guard portion 225 may reduce the influence of external noise, and thus, may reduce an influence of a parasitic capacitance.

A biosignal measured between the first electrode 210 and the second electrode 215 is transferred to the preamplifier 230. The preamplifier 230 converts the biosignal having a small intensity into a voltage signal having a high gain value based on a high input impedance. The preamplifier 230 outputs the biosignal of which noise is reduced, based on a differential input between a biosignal transferred from each of the first guard portion 220 and the second guard portion 225, and a biosignal transferred from each of the first electrode 210 and the second electrode 215. The shield 235 is connected to a ground, and is electrically separate from the first guard portion 220 and the second guard portion 225. The preamplifier 230 amplifies the biosignal measured between the first electrode 210 and the second electrode 215, and outputs the amplified biosignal.

FIGS. 3 through 6 are diagrams illustrating other examples of a bioelectrode. The examples of the bioelectrode having biosignal measuring electrodes that are not exposed externally are provided with reference to FIGS. 3 through 6.

Figure 3:
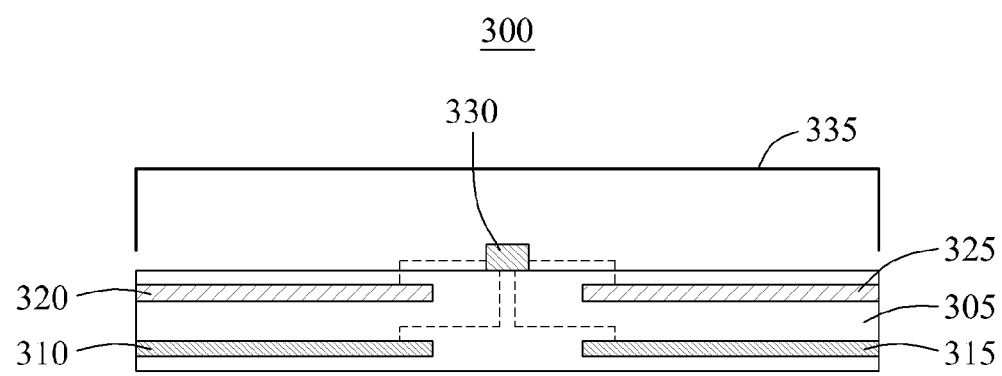
FIGS. 3 through 6 are diagrams illustrating other examples of a bioelectrode.

Referring to FIG. 3, a bioelectrode 300 includes a plate 305, a first electrode 310, a second electrode 315, a first guard portion 320, a second guard portion 325, a preamplifier 330, and a shield 335. The first electrode 310 and the second electrode 315 are disposed on an internal layer of a first side of the plate 305. The first electrode 310 and the second electrode 315 are disposed internally into the plate 305. The first electrode 310 and the second electrode 315 are disposed on an identical plane and disposed separate from one another. The first guard portion 310 and the second guard portion 325 are disposed on an internal layer of a second side of the plate 305. The first guard portion 320 and the second guard portion 325 are disposed internally into the plate 305. The first guard portion 320 and the second guard portion 325 are disposed on an identical plane and disposed separate from one another. The first electrode 310 and the first guard portion 320 are disposed vertically separate from one another. The second electrode 315 and the second guard portion 325 are disposed vertically separate from one another.

Figure 4:
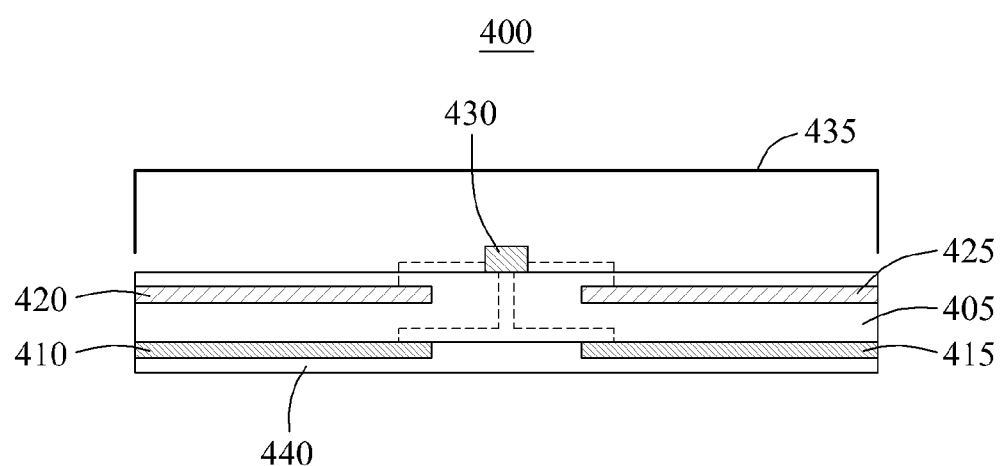

Referring to FIG. 4, a bioelectrode 400 includes a plate 405, a first electrode 410, a second electrode 415, a first guard portion 420, a second guard portion 425, a preamplifier 430, a shield 435, and a first insulation layer 440. The first electrode 410 and the second electrode 420 are disposed on a lower surface of a first side of the plate 405. The first electrode 410 and the second electrode 415 are disposed between the plate 405 and the first insulation layer 440. In each of the first electrode 410 and the second electrode 415, one surface comes into contact with the plate 405, and another surface comes into contact with the first insulation layer 440. The first guard portion 420 and the second guard portion 425 are disposed on an internal layer of a second side of the plate 405. The first guard portion 420 and the second guard portion 425 are disposed internally into the plate 405.

Figure 5:
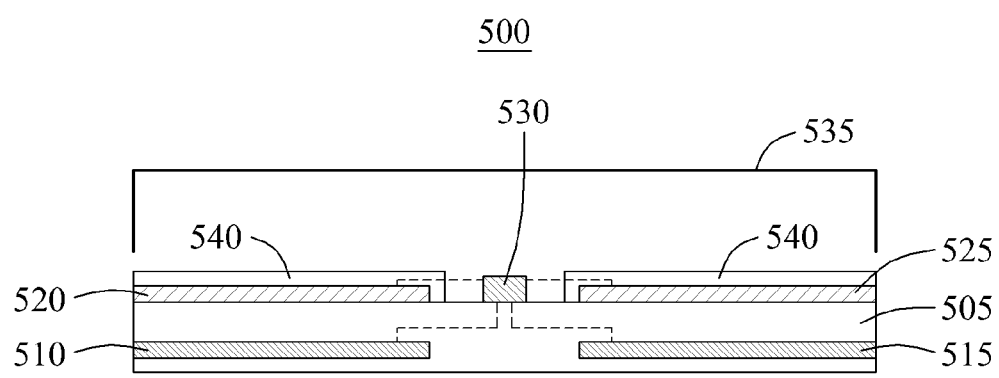

Referring to FIG. 5, a bioelectrode 500 includes a plate 505, a first electrode 510, a second electrode 515, a first guard portion 520, a second guard portion 525, a preamplifier 530, a shield 535, and a second insulation layer 540. The first electrode 510 and the second electrode 515 are disposed on an internal layer of a first side of the plate 505. The first electrode 510 and the second electrode 515 are disposed internally into the plate 505. The first guard portion 520 and the second guard portion 525 are disposed on an upper surface of a second side of the plate 505. The first guard portion 520 and the second guard portion 525 are disposed between the second insulation layer 540 and the plate 505. In each of the first guard portion 520 and the second guard portion 525, one surface comes into contact with the plate 505, and another surface comes into contact with the second insulation layer 540. The first guard portion 520 and the second guard portion 525 are disposed on an identical plane and disposed separate from one another.

Figure 6:
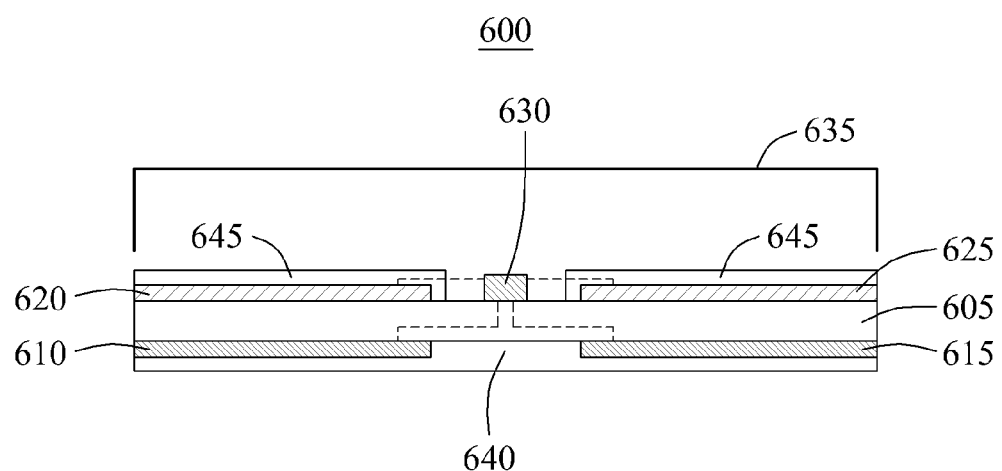

Referring to FIG. 6, a bioelectrode 600 includes a plate 605, a first electrode 610, a second electrode 615, a first guard portion 620, a second guard portion 625, a preamplifier 630, a shield 635, a first insulation layer 640 and a second insulation layer 645. The first electrode 610 and the second electrode 615 are disposed on a lower surface of a first side of the plate 605. The first electrode 610 and the second electrode 615 are disposed between the plate 605 and the first insulation layer 640. In each of the first electrode 610 and the second electrode 615, one surface comes into contact with the plate 605, and another surface comes into contact with the first insulation layer 640. The first electrode 610 and the second electrode 615 are disposed on an identical plane and disposed separate from one another. The first guard portion 620 and the second guard portion 625 are disposed on an upper surface of a second side of the plate 605. The first guard portion 620 and the second guard portion 625 are disposed between the second insulation layer 645 and the plate 605. In each of the first guard portion 620 and the second guard portion 625, one surface comes into contact with the plate 605, and another surface comes into contact with the second insulation layer 645. The first guard portion 620 and the second guard portion 625 are disposed on an identical plane and disposed separate from one another.

Figure 7:
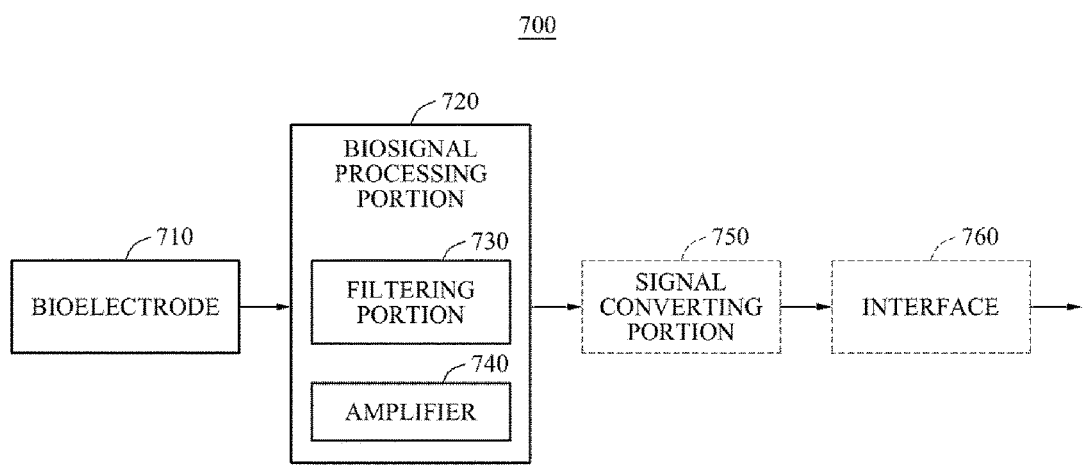
FIG. 7 is a block diagram illustrating an example of a biosignal processing apparatus.

FIG. 7 is a block diagram illustrating an example of a biosignal processing apparatus 700. The biosignal processing apparatus 700 amplifies a biosignal measured by a bioelectrode 710, and outputs the amplified biosignal. In an example, the biosignal processing apparatus 700 may operate in a wearable device provided in a form of, for example, a watch, a glove, clothes, a hat, glasses, and/or a shoe. The biosignal processing apparatus 700 may convert the biosignal into biometric data appropriate for processing by the wearable device, and transfer the biometric data to the wearable device. The wearable device may determine, for example, a gesture performed by a user and a psychological state, a health state, and a body state of the user based on the biometric data received from the biosignal processing apparatus 700.

For example, the gesture performed by the user may be determined based on an EMG signal measured from a body of the user. The bioelectrode 710 may measure the EMG signal from the body of the user. The biosignal processing apparatus 700 may amplify the EMG signal, and convert the amplified EMG signal into a digital signal. The digital signal converted from the EMG signal may be transferred to the wearable device. Based on the digital signal, the wearable device may determine the gesture performed by the user.

Referring to FIG. 7, the biosignal processing apparatus 700 includes a bioelectrode 710 and a biosignal processing portion 720. The bioelectrode 710 measures the biosignal without making direct electrical contact with the body of the user. The bioelectrode 710 may include a first electrode and a second electrode that are disposed on a first side of a plate and disposed separate from one another. Also, the bioelectrode 710 may include a first guard portion and the second guard portion that are disposed on a second side of the plate and disposed separate from one another. The first guard portion may be disposed to vertically overlap the first electrode, and the second guard portion may be disposed to vertically overlap the second electrode. The bioelectrode 710 may include a preamplifier that converts an infinitesimal biosignal measured between a plurality of electrodes, into a voltage signal having a high gain value. The bioelectrode 710 may include a shield disposed externally to the first guard portion and the second guard portion, and electrically separate from the first guard portion and the second guard portion.

The biosignal processing portion 720 includes a filtering portion 730 and an amplifier 740. The filtering portion 730 filters the biosignal output from the bioelectrode 710. The filtering portion 730 may include a high pass filter circuit, a band stop filter circuit, and/or a low pass filter circuit. The high pass filter circuit may be connected to an output end of the preamplifier of the bioelectrode 710, and the band stop filter circuit may be connected to an output end of the high pass filter circuit. The low pass filter circuit may be connected to an output end of the band stop filter circuit, and the amplifier 740 may be connected to an output end of the low pass filter circuit.

In an example, the high pass filter circuit may filter out an offset of a biosignal input through a displacement current. The band stop filter circuit may filter out common mode noise of a 60-hertz (Hz) frequency band from the biosignal output from the high pass filter circuit. The low pass filter circuit may output a signal of a frequency band less than or equal to 100 Hz, from the biosignal output from the band stop filter circuit.

The amplifier 740 amplifies the biosignal filtered by the filtering portion 730. The amplifier 740 may be an instrumentation amplifier, and may amplify the biosignal output from the filtering portion 730 based on a predetermined gain.

The biosignal processing apparatus 700 may also include a signal converting portion 750 and an interface 760. The signal converting portion 750 may convert the biosignal filtered and amplified in the biosignal processing portion 720, into a digital signal. The interface 760 transmits, to an external area, the digital signal converted from the biosignal.

Figure 8:
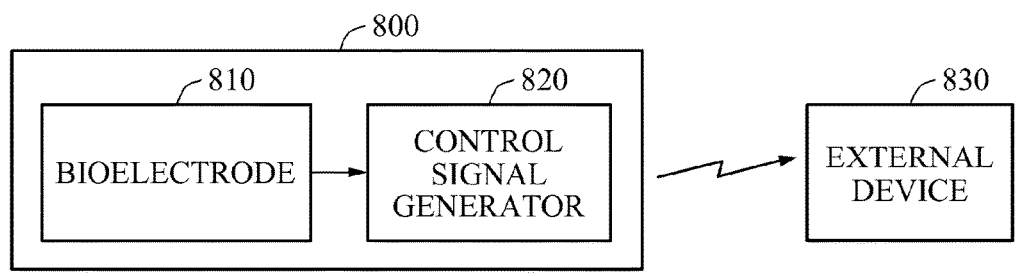
FIG. 8 is a diagram illustrating another example of a biosignal processing apparatus.

FIG. 8 is a diagram illustrating another example of a biosignal processing apparatus 800. The biosignal processing apparatus 800 generates a control signal used to control an external device 830 based on a biosignal measured by a bioelectrode 810, and transmits the generated control signal to the external device 830. In response to receiving the control signal, the external device 830 performs a predetermined control operation corresponding to the control signal. The biosignal processing apparatus 800 may operate in a wearable device.

Referring to FIG. 8, the biosignal processing apparatus 800 includes the bioelectrode 810 and a control signal generator 820. The bioelectrode 810 measures the biosignal using a plurality of electrodes disposed on a first side of a plate and disposed separate from one another, without making direct electrical contact with a body of a user. The bioelectrode 810 includes a plurality of guard portions disposed on a second side of the plate and disposed separate from one another. The bioelectrode 810 includes a preamplifier that outputs a voltage signal based on the biosignal measured between the electrodes, and a shield disposed externally to the plate.

The control signal generator 820 generates the control signal used to control the external device 830 based on the biosignal output from the bioelectrode 810. The external device 830 may include, for example, a mobile device, a personal computer (PC), and/or a multimedia device. The control signal generator 820 may analyze a level, a frequency property, and/or a waveform of the biosignal, and determine a control operation corresponding to the control signal. The control signal generator 820 generates a control signal to perform the determined control operation. The control signal generated by the control signal generator 820 is transmitted to the external device 830, and the external device 830 performs the control operation based on the control signal received from the biosignal processing apparatus 800.

Figure 9:
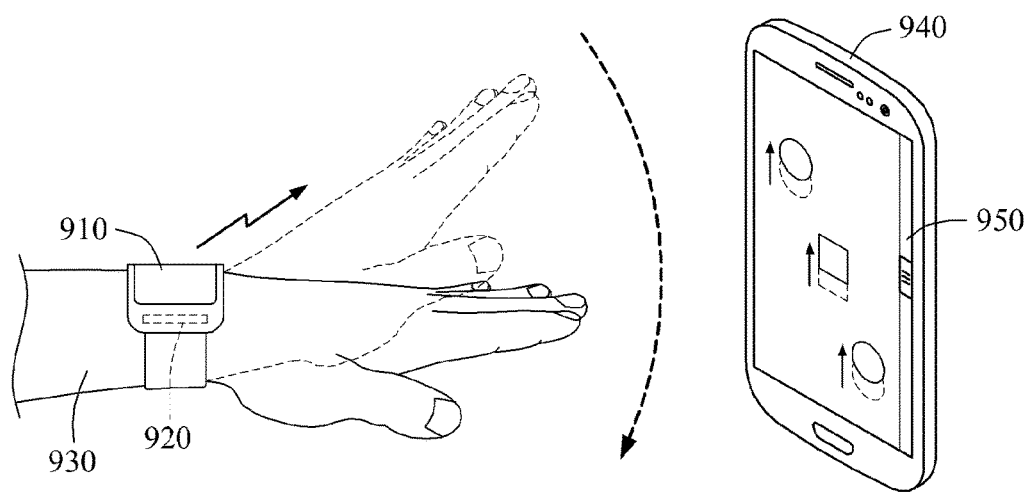
FIG. 9 is a diagram illustrating an example of a biosignal processing apparatus operating in a wearable device.

FIG. 9 is a diagram illustrating an example of a biosignal processing apparatus 920 operating in a wearable device 910. The biosignal processing apparatus 920 operates in the wearable device 910. The biosignal processing apparatus 920 measures an EMG signal of a user 930, and generates a control signal based on the measured EMG signal. For example, the user 930 may control an external device 940 to perform an operation corresponding to a predetermined gesture by performing the predetermined gesture in a state of wearing the wearable device 910 provided in a form of a watch including the biosignal processing apparatus 920. The biosignal processing apparatus 920 may measure an EMG signal change occurring in a process of performing the corresponding gesture, and analyze a result of the measuring. The biosignal processing apparatus 920 determines a control operation corresponding to the gesture performed by the user 930, and then generates the control signal to perform the determined control operation.

The wearable device 910 performs various interfaces based on the control signal generated by the biosignal processing apparatus 920. The wearable device 910 may display, on a screen, contents related to the control operation determined by the biosignal processing apparatus 920, or output the control operation in a form of a sound. In response to receiving a user input related to the control operation, or in response to determining the control operation corresponding to the EMG signal, the wearable device 910 may transmit the generated control signal to the external device 940. The control signal may be used to control an operation of the external device 940 communicating with the wearable device 910. Depending on a type of a control device, the wearable device 910 may be controlled by the control signal generated based on the EMG signal.

In an example, when the user 930 performs a gesture of lowering a hand down in the state of wearing the wearable device 910 provided in the form of the watch, the biosignal processing apparatus 920 may measure an EMG signal changed in wrist muscles, and generate a control signal based on the measured EMG signal. The biosignal processing apparatus 920 may filter the measured EMG signal, amplify the measured EMG signal, and/or convert the measured EMG signal into a digital signal. The biosignal processing apparatus 920 may analyze the EMG signal, and determine a control operation corresponding to the EMG signal. A control operation determined based on a type of the EMG signal may be determined and stored in advance.

The biosignal processing apparatus 920 may determine that the user 930 performs the gesture of lowering the hand by analyzing the EMG signal, and generate the control signal to perform the control operation corresponding to the gesture. The generated control signal may be transmitted to the external device 940, and the external device 940 may perform the control operation based on the control signal. For example, based on the control signal corresponding to the gesture of lowering the hand of the user 930, a scroll 950 of the external device 940 may be controlled such that the screen or the contents displayed on a display of the external device 940 moves in an upward direction. As another example, based on the control signal corresponding to the gesture of lowering the hand of the user 930, the contents displayed on the display of the external device 940 may be controlled, thereby implementing an interface of moving the contents in a downward direction of the display.

Figure 10:
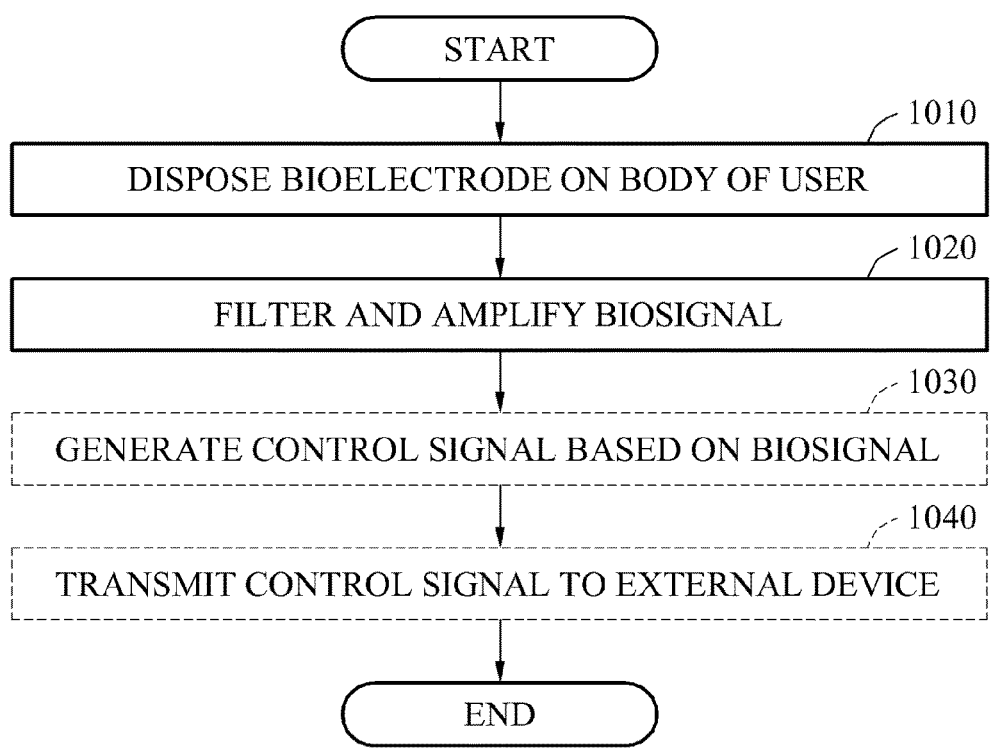
FIG. 10 is a flowchart illustrating an example of a biosignal processing method.

FIG. 10 is a flowchart illustrating an example of a biosignal processing method. In operation 1010, a bioelectrode is disposed on a body of a user. For example, the bioelectrode may be attached to a wrist or an arm of the user in a state in which the user is wearing clothes. The bioelectrode includes a plurality of electrodes disposed on a first side of a plate and disposed separate from one another, and a plurality of guard portions disposed on a second side of the plate and disposed separate from one another. The bioelectrode includes a preamplifier that converts an infinitesimal biosignal measured between the plurality of electrodes, into a voltage signal based on a high input impedance. The electrodes are electrically separate from the guard portions, and the bioelectrode includes a shield disposed externally to the preamplifier.

In operation 1020, the biosignal processing apparatus filters the biosignal measured between the plurality of electrodes in the bioelectrode, and amplifies the filtered biosignal. For example, the biosignal processing apparatus may filter out an offset of the biosignal, and/or then filter out common mode noise corresponding to a 60-Hz frequency band from the biosignal. Subsequently, the biosignal processing apparatus may output a signal of a frequency band less than or equal to 100 Hz from the biosignal. The biosignal processing apparatus amplifies the filtered biosignal using an amplifier. The biosignal processing apparatus converts the amplified biosignal into a digital signal, and outputs the digital signal.

The biosignal processing apparatus may selectively perform operation 1030. In operation 1030, the biosignal processing apparatus generates a control signal to control an external device based on the biosignal amplified in operation 1020. The biosignal processing apparatus may determine a control operation corresponding to the biosignal based on a level, a frequency, and/or a waveform of the biosignal, and then generate a control signal to perform the determined control operation.

The biosignal processing apparatus may selectively perform operation 1040. In operation 1040, the biosignal processing apparatus selectively transmits, to the external device, the control signal generated in operation 1030. In response to receiving the control signal, the external device may perform the control operation based on the control signal.

The apparatuses and portions described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The media may also include, alone or in combination with the software program instructions, data files, data structures, and the like. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

As a non-exhaustive illustration only, a device described herein may refer to mobile devices such as, for example, a cellular phone, a smart phone, a wearable smart device (such as, for example, a ring, a watch, a pair of glasses, a bracelet, an ankle bracket, a belt, a necklace, an earring, a headband, a helmet, a device embedded in the cloths or the like), a personal computer (PC), a tablet personal computer (tablet), a phablet, a personal digital assistant (PDA), a digital camera, a portable game console, an MP3 player, a portable/personal multimedia player (PMP), a handheld e-book, an ultra mobile personal computer (UMPC), a portable lab-top PC, a global positioning system (GPS) navigation, and devices such as a high definition television (HDTV), an optical disc player, a DVD player, a Blue-ray player, a setup box, or any other device capable of wireless communication or network communication consistent with that disclosed herein. In a non-exhaustive example, the wearable device may be self-mountable on the body of the user, such as, for example, the glasses or the bracelet. In another non-exhaustive example, the wearable device may be mounted on the body of the user through an attaching device, such as, for example, attaching a smart phone or a tablet to the arm of a user using an armband, or hanging the wearable device around the neck of a user using a lanyard.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:
1. A bioelectrode comprising:
   a plate having a first side and a second side, the first side being on an opposite side of the plate to the second side;

electrodes in direct contact with the first side of the plate, the electrodes having no contact with each other and being configured to measure a biosignal; and guard portions in direct contact with the second side of the plate directly opposite to the electrodes, the guard portions having no contact with each other and being configured to reduce external noise affecting the biosignal measured by the electrodes.

2. The bioelectrode of claim 1, wherein the electrodes comprise a first electrode disposed on the first side of the plate and a second electrode disposed on the first side of the plate and separate from the first electrode, and wherein the guard portions comprise a first guard portion disposed on the second side of the plate and a second guard portion disposed on the second side of the plate and separate from the first guard portion.

3. The bioelectrode of claim 2, wherein:

the first guard portion is disposed vertically separate from the first electrode; and the second guard portion is disposed vertically separate from the second electrode.

4. The bioelectrode of claim 2, wherein the first guard portion and the second guard portion are configured to reduce external noise affecting the biosignal measured between the first electrode and the second electrode.

5. The bioelectrode of claim 2, wherein the first electrode and the second electrode are configured to measure an electromyogram of a user without making direct electrical contact with a body of the user.

6. The bioelectrode of claim 1, further comprising:

a preamplifier configured to output a voltage signal based on the biosignal measured between the first electrode and the second electrode.

7. The bioelectrode of claim 6, wherein the first guard portion and the second guard portion comprise a conductive material, and are electrically connected to the preamplifier.

8. The bioelectrode of claim 1, further comprising:

a shield disposed externally to the preamplifier, the first guard portion, and the second guard portion adjacent to the second side of the plate.

9. The bioelectrode of claim 8, wherein the shield is configured to form an air layer between the shield and the plate.

10. The bioelectrode of claim 8, wherein the shield comprises a conductive material, and is connected to a ground.

11. The bioelectrode of claim 1, wherein one of the electrodes and the guard portions are disposed between the plate and an insulation layer.

12. The bioelectrode of claim 1, wherein one of the electrodes and the guard portions are disposed internally into the plate.

13. A biosignal processing apparatus comprising:

a bioelectrode configured to measure a biosignal without making direct electrical contact with a body of a user; and a biosignal processing portion configured to filter the biosignal, and amplify the filtered biosignal, wherein the bioelectrode comprises:

a plate having a first side and a second side, the first side being on an opposite side of the plate to the second side;

electrodes in direct physical contact with the first side of the plate and having no contact with each other, the biosignal being measured between the electrodes; and guard portions in direct physical contact with the second side of the plate and having no contact with each other, wherein the guard portions are positioned directly opposite to the electrodes and are configured to reduce external noise affecting the biosignal measured between the electrodes.

14. The apparatus of claim 13, wherein:

the electrodes comprise a first electrode and a second electrode;

the guard portions comprise a first guard portion and a second guard portion;

the first guard portion is disposed to vertically overlap the first electrode; and the second guard portion is disposed to vertically overlap the second electrode.

15. The apparatus of claim 14, further comprising:

a signal converter configured to convert the biosignal output from the biosignal processing portion, into a digital signal; and an interface configured to transmit the digital signal to an external area.

16. The apparatus of claim 13, wherein the bioelectrode further comprises:

a preamplifier configured to output a voltage signal based on a biosignal measured between the electrodes based on an input impedance.

17. The apparatus of claim 13, wherein the bioelectrode further comprises a shield disposed externally to the guard portions and electrically separate from the guard portions.

18. The apparatus of claim 13, wherein the biosignal processing apparatus is configured to operate in a wearable device.

19. A biosignal processing apparatus comprising:

a bioelectrode configured to measure a biosignal without making direct electrical contact with a body of a user; and a control signal generator configured to generate a control signal to be used to control an external device based on the biosignal, wherein the bioelectrode comprises:

a plate having a first side and a second side, the first side being on an opposite side of the plate to the second side;

electrodes in direct physical contact with the first side of the plate and having no contact with one another, the biosignal being measured between the electrodes;

guard portions in direct physical contact with the second side of the plate and having no contact with one another; the guard portions being positioned directly opposite to the electrodes and being configured to reduce external noise affecting the biosignal measured between the electrodes;

a preamplifier in direct physical contact with the first side of the plate and electrically connected to electrodes, the preamplifier being configured to amplify the biosignal measured between the electrodes; and a shield positioned adjacent to the second side of the plate with no direct physical contact with the plate or electrodes, the shield being configured to reduce external noise affecting the biosignal measured between electrodes.

20. The apparatus of claim 19, wherein the guard portions are composed of a conductive material, and are electrically connected to the preamplifier; and the shield is composed of a conductive material and connected to a ground.

* * * * *